US006294182B1

United States Patent
Znaiden et al.

(10) Patent No.: US 6,294,182 B1
(45) Date of Patent: Sep. 25, 2001

(54) TOWELETTE PRODUCT FOR MINIMIZING FACIAL FINE LINES AND WRINKLES

(75) Inventors: Alexander Paul Znaiden, Trumball; Craig Stephen Slavtcheff, Guilford; Robert Edward Gott, Norwalk, all of CT (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/425,713

(22) Filed: Oct. 22, 1999

Related U.S. Application Data

(60) Provisional application No. 60/124,960, filed on Mar. 18, 1999.

(51) Int. Cl.$^7$ .............................. A61K 6/00; A61K 7/00; A61K 9/00; A01N 25/34
(52) U.S. Cl. ........................... 424/402; 424/400; 424/401
(58) Field of Search .................................. 424/400, 401, 424/402

(56) References Cited

U.S. PATENT DOCUMENTS

| | | | |
|---|---|---|---|
| 4,725,489 | * 2/1988 | Jones et al. ........................ | 428/289 |
| 4,764,418 | 8/1988 | Kuenn et al. ...................... | 428/284 |
| 4,828,912 | 5/1989 | Hossain et al. .................... | 428/289 |
| 4,904,524 | 2/1990 | Yoh ................................... | 428/311.3 |
| 4,975,217 | 12/1990 | Brown-Skrobot et al. .......... | 252/107 |
| 5,017,365 | 5/1991 | Niedbala ............................ | 424/59 |
| 5,049,440 | 9/1991 | Bornhoeft, II et al. ............ | 428/288 |
| 5,091,171 | 2/1992 | Yu et al. ............................ | 424/642 |
| 5,196,187 | * 3/1993 | Nicoll et al. ........................ | 424/70 |
| 5,505,948 | 4/1996 | Rapaport ........................... | 424/401 |
| 5,534,265 | 7/1996 | Fowler et al. ..................... | 424/489 |
| 5,554,597 | 9/1996 | Yu et al. ............................ | 424/557 |
| 5,554,652 | 9/1996 | Yu et al. ............................ | 514/557 |
| 5,561,158 | 10/1996 | Yu et al. ............................ | 514/557 |
| 5,620,694 | 4/1997 | Girardot ............................ | 424/402 |
| 5,716,625 | 2/1998 | Hahn et al. ........................ | 424/401 |
| 5,720,961 | 2/1998 | Fowler et al. ..................... | 424/401 |
| 5,730,991 | 3/1998 | Rapaport ........................... | 424/401 |
| 5,744,149 | 4/1998 | Girardot ............................ | 424/401 |
| 5,756,107 | 5/1998 | Hahn et al. ........................ | 424/401 |
| 5,776,473 | 7/1998 | Perricone et al. ................. | 424/401 |
| 5,811,108 | 9/1998 | Goeringer ......................... | 424/401 |
| 5,814,662 | 9/1998 | Znaiden et al. ................... | 514/557 |
| 5,942,250 | 8/1999 | Yu et al. ............................ | 424/481 |
| 5,951,991 | 9/1999 | Wagner et al. .................... | 424/401 |
| 5,958,436 | 9/1999 | Hahn et al. ........................ | 424/401 |
| 5,965,616 | 10/1999 | Wang et al. ....................... | 514/557 |
| 5,972,360 | 10/1999 | Braun ................................ | 424/401 |
| 5,980,924 | 11/1999 | Yamazaki et al. ................. | 424/402 |
| 5,985,300 | 11/1999 | Crotty et al. ...................... | 424/402 |
| 5,993,832 | 11/1999 | Lorant et al. ..................... | 424/401 |
| 6,054,120 | 4/2000 | Burgoyne et al. ................. | 424/59 |
| 6,063,390 | 5/2000 | Farrell et al. ..................... | 424/404 |
| 6,063,397 | 5/2000 | Fowler et al. ..................... | 424/443 |
| 6,074,630 | 6/2000 | Devillez et al. ................... | 424/59 |
| 6,106,818 | 8/2000 | Dulog et al. ...................... | 424/78.03 |
| 6,110,205 | 8/2000 | Niles ................................. | 623/11.11 |

FOREIGN PATENT DOCUMENTS

| | | |
|---|---|---|
| 0 508 324 | 4/1992 | (EP) . |
| 3291206 | 12/1991 | (JP) . |
| 96/11572 | 4/1996 | (WO) . |
| 99/66793 | 12/1999 | (WO) . |

* cited by examiner

Primary Examiner—Thurman K. Page
Assistant Examiner—S. Howard
(74) Attorney, Agent, or Firm—Milton L. Honig

(57) ABSTRACT

A disposable towelette is provided which includes a flexible substrate such as a cellulosic tissue impregnated with an alpha-hydroxycarboxylic add delivered in a cosmetically acceptable carrier vehicle. There is further provided a method for cleansing skin and simultaneously inhibiting fine lines and wrinkles by wiping the skin with the impregnated towelette.

9 Claims, No Drawings

TOWELETTE PRODUCT FOR MINIMIZING FACIAL FINE LINES AND WRINKLES

This application claim benefit to provisional application 60/124,960 filed Mar. 18, 1999.

BACKGROUND OF THE INVENTION

1. Field of the Invention

The invention concerns single use towelettes for cosmetically controlling facial fine lines and wrinkles.

2. The Related Art

Forever young. Adults as they age seek to preserve the indicia of youth. Through the ages cosmetics have proved valuable for retarding the signs of the aging process. Facial foundations, creams and lotions have all helped in the coverup. Yet few really effective actives are available in the cosmetic chemist's arsenal. One of the few effective actives are a class of materials known as alpha-hydroxycarboxylic acids.

U.S. Pat. No. 5,091,171 (Yu et al.) was one of the first documents describing the use of alpha-hydroxycarboxylic acids as being effective against the appearance of fine lines and wrinkles. Subsequent thereto a vast literature and many commercial products were generated based on the efficacy of these materials. Most often the formulations were of the cream or lotion type. One problem with these formulations is that they do not always evenly distribute over the applied surfaces. Secondly, any time an active treated surface is followed by a cleansing, the active washes away. Methods to maintain alpha-hydroxycarboxylic acids on a skin surface are needed which are not as susceptible to subsequent cleansing actions. Irritation has also been of great concern because the formulations are generally of low pH.

WO 96/11572 (Moberg) has utilized a variety of acids including the alpha-hydroxy substance known as lactic acid in an aqueous hexylene glycol formula impregnated onto textiles or refreshing napkins. These were employed to overcome the problem of microbial growth on skin and served as a disinfection treatment.

Accordingly, it is an object of the present invention to provide a product and method for both cleansing skin and reducing the signs of aging including controlling formation of fine lines and wrinkles.

Another object of the present invention is to provide a product and method in which actives that control fine lines and wrinkles maintain their presence on the skin even after a cleansing treatment.

Still another object of the present invention is to provide a product and method for controlling the signs of aging, especially those of fine lines and wrinkles while minimizing irritation often associated with such actives.

These and other objects of the present invention will become more apparent from the following summary and detailed discussion which follow.

SUMMARY OF THE INVENTION

A disposable towelette product is provided for cleansing and managing signs of aging on the skin, the product including:
(a) a container housing a towelette which includes:
  (i) a substrate;
  (ii) an alpha-hydroxycarboxylic acid; and
  (iii) a cosmetically acceptable vehicle for impregnating the alpha-hydroxycarboxylic acid as a composition onto the substrate;
(b) written instructions on the package on use of the towelette against the skin to achieve a reduction in the signs of aging.

A method is also provided for cleansing and managing the signs of aging on skin, the method including:
(a) providing a towelette which is constituted of:
  (i) a substrate;
  (ii) an alpha-hydroxycarboxylic acid;
  (iii) a cosmetically acceptable vehicle for impregnating the alpha-hydroxycarboxylic acid as a composition onto the substrate; and
(b) wiping the surface of the skin with the towelette.

DETAILED DESCRIPTION OF THE INVENTION

Now it has been found that towelettes impregnated with alpha-hydroxycarboxylic acids allow for a combined cleansing and anti-aging treatment of the skin. Since cleansing with a towelette requires no wash-off step, the alpha-hydroxycarboxylic acid can deposit in amounts and remain deposited just as if the active were delivered via a cream or lotion. The uniformly impregnated towelettes distribute the active on the skin in a much more even manner than cream, lotion, gel or stick products.

A first necessary aspect of the present invention is that of a substrate. Preferably the substrate is a water insoluble substance. By "water insoluble" is meant the substrate does not dissolve in or readily break apart upon immersion in water. Another advantage of the substrate in combination with the active is that the former helps the active penetrate. The substrate is also much better than a mere liquid or gel formulation in the accurate application to the skin and avoidance of sensitive areas such as inadvertently directing the astringent composition to areas of the eye thereby irritating same.

A wide variety of materials can be used as the substrate. The following nonlimiting characteristics are desirable: (I) sufficient wet strength for use, (ii) sufficient abrasivity, (iii) sufficient loft and porosity, (iv) sufficient thickness, (v) appropriate size, and (vi) non-reactive with components of the impregnating composition.

Nonlimiting examples of suitable substrates which meet the above criteria include nonwoven substrates, woven substrates, hydroentangled substrates, air entangled substrates and the like. Preferred embodiments employ nonwoven substrates since they are economical and readily available in a variety of materials. By nonwoven is meant that the layer is comprised of fibers which are not woven into a fabric but rather are formed into a sheet, particularly a tissue. The fibers can either be random (i.e., randomly aligned) or they can be carded (i.e. combed to be oriented in primarily one direction). Furthermore, the nonwoven substrate can be composed of a combination of layers of random and carded fibers.

Nonwoven substrates may be comprised of a variety of materials both natural and synthetic. By natural is meant that the materials are derived from plants, animals, insects or byproducts. By synthetic is meant that the materials are obtained primarily from various man-made materials or from material that is usually a fibrous web comprising any of the common synthetic or natural textile-length fibers, or mixtures thereof.

Nonlimiting examples of natural materials useful in the present invention are silk fibers, keratin fibers and cellulosic fibers. Nonlimiting examples of keratin fibers include those selected from the group consisting of wool fibers, camel hair fibers, and the like. Nonlimiting examples of cellulosic fibers include those selected from the group consisting of wood pulp fibers, cotton fibers, hemp fibers, jute fibers, flax fibers, and mixtures thereof. Wood pulp fibers are preferred while all cotton fibers (e.g. cotton pads) are normally avoided.

Nonlimiting examples of synthetic materials useful in the present invention include those selected from the group consisting of acetate fibers, acrylic fibers, cellulose ester fibers, modacrylic fibers, polyamide fibers, polyester fibers, polyolefin fibers, polyvinyl alcohol fibers, rayon fibers and mixtures thereof. Examples of some of these synthetic materials include acrylics such as Acrilan®, Creslan®, and the acrylonitrile-based fiber, Orion®; cellulose ester fibers such as cellulose acetate, Arnel®, and Acele®; polyamides such as Nylons (e.g., Nylon 6, Nylon 66, Nylon 610 and the like); polyesters such as Fortrel®, Kodel®, and the polyethylene terephthalate fibers, Dacron®; polyolefins such as polypropylene, polyethylene; polyvinyl acetate fibers and mixtures thereof.

Nonwoven substrates made from natural materials consist of webs or sheets most commonly formed on a fine wire screen from a liquid suspension of the fibers.

Substrates made from natural materials useful in the present invention can be obtained from a wide variety of commercial sources. Nonlimiting examples of suitable commercially available paper layers useful herein include Airtex®, an embossed airlaid cellulosic layer having a base weight of about 71 gsy, available from James River Corporation, Green Bay, Wis.; and Walkisoft®, an embossed airlaid cellulosic having a base weight of about 75 gsy, available from Walkisoft U.S.A., Mount Holly, N.C.

Nonwoven substrates made from synthetic materials useful in the present invention can also be obtained from a wide variety of commercial sources. Nonlimiting examples of suitable nonwoven layer materials useful herein include HEF 40-047, an apertured hydroentangled material containing about 50% rayon and 50% polyester, and having a basis weight of about 43 grams per square yard (gsy), available from Veratec, Inc., Walpole, Mass.; HEF 140-102, an apertured hydroentangled material containing about 50% rayon and 50% polyester, and having a basis weight of about 56 gsy, available from Veratec, Inc., Walpole, Mass.; Novenet® 149-191, a thermo-bonded grid patterned material containing about 69% rayon, about 25% polypropylene, and about 6% cotton, and having a basis weight of about 100 gsy, available from Veratec, Inc., Walpole, Mass.; HEF Nubtex® 149-801, a nubbed, apertured hydroentangled material, containing about 100% polyester, and having a basis weight of about 70 gsy, available from Veratec, Inc. Walpole, Mass.; Keybak®951V, a dry formed apertured material, containing about 75% rayon, about 25% acrylic fibers, and having a basis weight of about 43 gsy, available from Chicopee Corporation, New Brunswick, N.J.; Keybak® 1368, an apertured material, containing about 75% rayon, about 5% polyester, and having a basis weight of about 39 gsy, available from Chicopee Corporation, New Brunswick, N.J.; Duralace® 1236, an apertured, hydroentangled material, containing about 100% rayon, and having a basis weight from about 40 gsy to about 115 gsy, available from Chicopee Corporation, New Brunswick, N.J.; Duralace® 5904, an apertured, hydroentangled material, containing about 100% polyester, and having a basis weight from about 40 gsy to about 115 gsy, available from Chicopee Corporation, New Brunswick, N.J.; Sontaro® 8868, a hydroentangled material, containing about 50% cellulose and about 50% polyester, and having a basis weight of about 60 gsy, available from Dupont Chemical Corp.

Most preferred as a towelette for purposes of this invention are non-woven substrates, especially blends of rayon/polyester and ratios of 10:90 to 90:10, preferably ratios of 20:80 to 80:20, optimally 40:60 to 60:40 by weight. A most useful towelette is a 70:30 rayon/polyester non-woven wipe article.

The substrate can be made into a wide variety of shapes and forms. Generally the substrate is in single use towelette form. Advantageously, the towelettes are folded in a Z-shaped formation. They may be interleaved with one another but preferably are not interleaved. The Z fold consists of a center panel flanked by upper and lower wing panels. The upper and lower wing panels are substantially of equal width and substantially half of a width of the center panel. Each towelette is folded medially in a direction orthogonal to that of the Z-shaped formation. Advantageously the size of the towelette may range in length from 10 to 40 cm, preferably from 15 to 30 cm, optimally from 18 to 24 cm. The width of the towelette may range from 8 to 30 cm, preferably from 10 to 25 cm, optimally from 15 to 20 cm.

Anywhere from 5 to 100, preferably from 10 to 50 single towelettes may be stored within a dispensing pouch, preferably a moisture impermeable pouch. During storage and between dispensing, the pouch is resealable, usually via an adhesive strip covering a dispensing opening. Single towelette containing pouches may also be employed.

The substrates of the present invention can comprise two or more layers, each having a different texture and abrasiveness. The differing textures can result from the use of different combinations of materials or from the use of a substrate having a more abrasive side for exfoliation and a softer, absorbent side for gentle cleansing. In addition, separate layers of the substrate can be manufactured to have different colors, thereby helping the user to further distinguish the surfaces.

A second important element of the present invention is that of an alpha-hydroxycarboxylic acid. By this term is meant not only the acid form but also salts thereof. Typical cationic counterions to form the salt are the alkali metals, alkaline earth metals, ammonium, $C_2$–$C_8$ trialkanolammonium cation and mixtures thereof. The term "alpha-hydroxycarboxylic acids" include not only hydroxyacids but also alpha-ketoacids and related compounds of polymeric forms of hydroxyacid.

Hydroxyacids are organic carboxylic acids in which one hydroxyl group is attached to the alpha carbon adjacent the carboxy group. The generic structure is as follows:

(Ra)(Rb)C(OH)COOH where Ra and Rb are H, F, Cl, Br, alkyl, aralkyl or aryl group of saturated or unsaturated, isomeric or non-isomeric, straight or branched chain or cyclic form, having 1 to 25 carbon atoms, and in addition Ra and Rb may carry OH, CHO, COOH and alkoxy groups having 1 to 9 carbon atoms. The alpha-hydroxyacids may be present as a free acid or in lactone form, or in a salt form with an organic base or an inorganic alkali. The alpha-hydroxyacids may exist as stereoisomers as D, L, and DL forms when Ra and Rb are not identical.

Typical alkyl, aralkyl and aryl groups for Ra and Rb include methyl, ethyl, propyl, isopropyl, butyl, pentyl, octyl, lauryl, stearyl, benzyl and phenyl, etc. The alpha-hydroxyacids of the first group may be sub-divided into (1) alkyl alpha-hydroxyacids, (2) aralkyl and aryl alpha-hydroxyacids, (3) polyhydroxy alpha-hydroxyacids, and (4)

polycarboxylic alpha-hydroxyacids. The following are representative alpha hydroxyacids in each subgroup.

(1) Alkyl Alpha Hydroxyacids

2-Hydroxyethancic acid (Glycolic acid, hydroxyacetic acid)
2-Hydroxypropanoic acid (Lactic acid)
2-Methyl 2-hydroxypropanoic acid (Methyllactic acid)
2-Hydroxybutanoic acid
2-Hydroxypentanoic acid
2-Hydroxyhexanoic acid
2-Hydroxyheptanoic acid
2-Hydroxyohtanoic acid
2-Hyroxynonanoic acid
2-Hydroxydecanoic acid
2-hydroxyundecanoic acid
2-Hydroxydodecanoic acid (Alpha hydroxylauric acid)
2-Hydroxytetradecanoic acid (Alpha hydroxymyristic acid)
2-Hydroxyhexadecanoic acid (Alpha hydroxypalmitic acid)
2-Hydroxyoctadecanoic acid (Alpha hydroxystearic acid)
2-Hydroxyeicosanoic acid (Alpha hydroxyarachidonic acid)

(2) Aralkyl And Aryl Alpha-Hydroxyacids

2-Phenyl 2-hydroxyethanoic acid (Mandelic acid)
2,2-Diphenyl 2-hydroxyethanoic acid (Benzilic acid)
3-Phenyl 2-hydroxypropanoic acid (Phenyllactic acid)
2-Phenyl 2-methyl 2-hydroxyethanoic acid (Atrolactic acid)
2-(4'-Hydroxyphenyl) 2-hydroxyethanoic acid (4-Hydroxymandelic add)
2-(4'-Chlorophenyl) 2-hydroxyethanoic acid (4-Chloromandelic acid)
2-(3'-Hydroxy-4'-methoxyphenyl) 2-hydroxyethanoic acid (3-Hydroxy-4-methoxymandelic acid)
2-(4'-Hydroxy-3'-methoxyphenyl acid)
3-(2'-Hydroxyphenyl) 2-hydroxypropanoic acid [3(2'Hydroxyphenyl) lactic acid]
3-(4'-Hydroxyphenyl) 2-hydroxypropanoic acid [3-(4'-Hydroxyphenyl) lactic acid]
2-(3',4'-Dihydroxyphenyl) 2-hydroxyethanoic acid (3,4-Dihydroxymandelic acid)

(3) Polyhydroxy Alpha-Hydroxyacids 2,3-Dihydroxypropanoic acid (Glyceric acid)
2,3,4-Trihydroxybutanoic acid, Isomers; erythronic acid, threonic acid)
2,3,4,5-Tetrahydroxypentanoic acid (Isomers; ribonic acid, arabinoic acid, xylonic acid, lyxonic acid)
2,3,4,5,6-Pentahydroxyhexanic acid (Isomers; allonic acid, altronic acid, gluconic acid, mannoic acid, gulonic acid, idonic acid, galatconic acid, talonic acid)
2,3,4,5,6,7-Hexahydroxyheptanoic acid (Isomers; glucoheptonic acid, galactoheptonic acid etc.)

(4) Polycarboxylic Alpha-Hydroxyacids

2-Hydroxypropane-1,3-dioic acid (Tartronic acid)
2-Hydroxybutane,1,4-dioic acid (Malic acid)
2,3-Dihydroxybutane-1,4-dioic acid (Tartaric acid)
2-Hydroxy-2-carboxypentane,1,5-dioic acid (Citric acid)
2,3,4,5-Tetrahydroxyhexane,1-5,dioic acid (Isomers: saccharic acid, mucic acid)

(5) Lactone Forms

The typical lactone forms are gluconolactone, galactonolactone, glucuronolactone, glacturonolactone, gluconolactone, ribonolactone, saccharic acid lactone, pantoyllactone, glucoheptonolactone, mannonolactone, and galactoheptonolactone.

Representative alpha ketoacids useful for the present invention are as follows.

2-Ketoethanoic acid (Glyoxylic acid)
Methyl 2-ketoethanoate
2-Ketopropanoic acid (Pyruvic acid)
Methyl 2-ketopropanoate (Methyl pyruvate)
Ethyl 2-ketopropanoate (Ethyl pyruvate)
Propyl 2ketopropanoate (Propyl pyruvate)
2-Phenyl-2-ketoethanoic acid (Benzoylformic acid)
Methyl 2-phenyl-2-ketoethanoate (Methyl benzoylformate)
Ethyl 2-phenyl-2-ketoethanoate (Ethyl benzoylformate)
3-Phenyl-2-ketopropanoic acid (Phenylpyruvic acid)
Methyl 3-phenyl-2-ketopropanoate (Methyl phenylpyruvate)
Ethyl 3-phenyl-2-ketopropanoate (Ethyl phenylpyruvate)
2-Ketobutanoic acid
2-Ketopentanoic acid
2-Ketohexanoic acid
2-Ketoheptanoic acid
2-Ketooctanoic acid
2-Ketododecanoic acid
Methyl 2-ketooctanoate II. Dimeric and Polymeric Forms of Hydroxyacids When two or more molecules of hydroxycarboxylic acids either identical or non-identical compounds are reacted chemically to each other, dimeric or polymeric compounds will be formed. Such dimeric and polymeric compounds may be classified into three groups, namely (a) acyclic ester, (b) cyclic ester and (c) miscellaneous dimer and polymer.

Representative acrylic esters of hydroxycarboxylic acids useful for the present invention are those found below.

Glycosyl glycollate (Glycolic acid glycollate)
Lactyl lactate (Lactic acid lactate)
Mandelyl mandellate
Atrolactyl atrolactate
Phenyllactyl phenyllactate
Benzilyl benzillate
Glycolyl lactate
Lactyl glycollate
Glycolyl glycolyl glycollate
Lactyl lactyl lactate
Lactyl glycolyl lactate
Glycolyl glycolyl glycolyl glycollate
Lactyl lactyl lactyl lactate
Glycolyl lactyl glycolyl lactyl glycollate
Polyglycolic acid and polylactic acid Amounts of the alpha-hydroxycarboxylic acids may range from about 0.01 to about 20%, preferably from about 0.1 to about 15%, more preferably from about 1 to about 10%, optimally from about 3 to about 8% by weight of the composition which impregnates the substrate.

The amount of impregnating composition relative to the substrate may range from about 20:1 to 1:20, preferably from 10:1 to about 1:10 and optimally from about 2:1 to about 1:2 by weight.

A humectant ordinarily is incorporated with compositions of the present invention. Humectants are normally polyols. Representative polyols include glycerin, diglycerin, polyalkylene glycols and more preferably alkylene polyols and their derivatives including propylene glycol, dipropylene glycol, polypropylene glycol, polyethylene glycol and derivatives thereof, sorbitol, hydroxypropyl sorbitol, hexylene glycol, 1,2-butylene glycol, 1,2,6-hexanetriol, isoprene glycol, ethoxylated glycerol, propoxylated glycerol and mixtures thereof. The most preferred is 2-methyl-1,3-propanediol available as MP Diol from the Arco Chemical Company. Amounts of the polyol may range from about 0.5 to about 95%, preferably from about 1 to about 50%, more preferably from about 1.5 to 20%, optimally from about 3 to about 10% by weight of the impregnating composition.

A variety of cosmetically acceptable carrier vehicles may be employed although the carrier vehicle normally will be water. Amounts of the carrier vehicle may range from about 0.5 to about 99%, preferably from about 1 to about 80%, more preferably from about 50 to about 70%, optimally from about 65 to 75% by weight of the impregnating composition.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the composition. Preservatives are preferably employed in amounts ranging from 0.01% to 2% by weight of the composition.

Compositions of the present invention may further include herbal extracts. Illustrative extracts include Roman Chamomile, Green Tea, Scullcap, Nettle Root, Swertia Iaponica, Fennel and Aloe Vera extracts. Amount of each of the extracts may range from about 0.001 to about 1%, preferably from about 0.01 to about 0.5%, optimally from about 0.05 to about 0.2% by weight of a composition.

Minor adjunct ingredients may also be present in the compositions. Among these may be vitamins such as Vitamin E Acetate, Vitamin C, Vitamin A Palmitate, Panthenol and any of the Vitamin B complexes. Anti-irritant agents may also be present including those of steviosides, alpha-bisabolol and glycyhrizzinate salts, each vitamin or anti-irritant agent being present in amounts ranging from about 0.001 to about 1.0%, preferably from about 0.01 to about 0.3% by weight of the composition.

Emulsifiers may also be incorporated into compositions of this invention. These emulsifiers may be anionic, nonionic, cationic, amphoteric and combinations thereof. Useful nonionic type emulsifiers include the $C_{10}$–$C_{20}$ fatty alcohol or acid hydrophobes condensed with from 2 to 100 moles of ethylene oxide or propylene oxide per mole of hydrophobe; $C_2$–$C_{10}$ alkyl phenols condensed with from 2 to 20 moles of alkylene oxide; mono- and di-fatty acid esters of ethylene glycol; fatty acid monoglyceride; sorbitan, mono- and di-$C_8$–$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic emulsifiers. Particularly preferred as the emulsifier is a hydrogenated castor wax alkoxylated with 40 moles ethylene oxide, available commercially as Cremophore RH-40®.

Mild emulsifiers of the anionic and amphoteric type may also be employed. Particularly preferred anionic examples include lauroamphoacetate salts and sarcosinate salts. Preferred amphoterics include cocamidopropylbetaine and dimethylbetaine.

Advantageously it may be desirable to avoid the presence of any emulsifiers or surfactants because these actives interact with the skin to accentuate irritation normally occurring with alpha-hydroxycarboxylic acids. Emulsifiers and surfactants tend to break the lipid barrier of the skin.

Amounts of the emulsifiers may range from about 0.05 to about 20%, preferably from about 0.1 to about 5%, optimally from about 0.5 to about 0.8% by weight.

These impregnating compositions of the present invention may involve a range of pH although it is preferred to have a relatively low pH, for instance, a pH from about 2 to about 6.5, preferably from about 2.5 to about 4.5.

Impregnating compositions of the present invention may also include silicones of a volatile and non-volatile variety. Typical volatile silicones are the cydomethicones commercially available as Dow Corning 244, 245, 344 and 345. linear volatile dimethicones are also suitable. Non-volatile silicones include polydimethyl siloxanes of a viscosity greater than 2 centistoke and silicone copolyols also known as dimethicone copolyol for which Dow Corning 193 is a commercial source. Amounts of the silicones may range from about 0.01 to about 20%, preferably from about 0.5 to about 3% by weight of the impregnating composition. Stickiness generated by such alpha-hydroxycarboxylic acids as ammonium glycolate are reduced by the presence of dimethicone copolyol.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated.

EXAMPLES 1–8

Table I provides a listing of formulations which are suitable for impregnation into a cellulosic substrate forming a towelette. The pH of the resulting composition solutions range from about 2.8 to about 4.0.

TABLE I

| INGREDIENT | EXAMPLE (WEIGHT %) | | | | | | | |
| --- | --- | --- | --- | --- | --- | --- | --- | --- |
| | 1 | 2 | 3 | 4 | 5 | 6 | 7 | 8 |
| Water | To 100 | To 100 | To 100 | To 100 | To 100 | To 100 | To 100 | To 100 |
| Glycolic Acid (70% Active) | 11.40 | — | — | — | 10.90 | 10.90 | 1.10 | — |
| Potassium Lactate | — | 8.00 | — | — | — | 0.50 | — | 4.00 |
| Alpha-Hydroxy-octanoic Acid | — | — | 0.50 | — | 0.50 | — | — | — |
| Glucarolactone | — | — | — | 2.00 | — | — | — | — |
| Ammonia Solution (30% Active) | 3.50 | — | — | — | 3.00 | 3.00 | 0.35 | — |
| Glycerin | 1.00 | 1.00 | 1.00 | 1.00 | 1.00 | 1.00 | 1.00 | 1.00 |
| Dimethicone Copolyol | 0.75 | 0.75 | 0.75 | 0.75 | 0.75 | 0.75 | 0.75 | 0.75 |
| Disodium Capryl-ampho-diacetate | 1.00 | 1.00 | 1.00 | 1.00 | 1.00 | 1.00 | 1.00 | 1.00 |
| Witch Hazel Extract | 0.50 | 0.50 | 0.50 | 0.50 | 0.50 | 0.50 | 0.50 | 0.50 |
| Glydant Plus | 0.20 | 0.20 | 0.20 | 0.20 | 0.20 | 0.20 | 0.20 | 0.20 |
| PEG-40 Hydrogenated Castor Oil | 0.50 | 0.50 | 0.50 | 0.50 | 0.50 | 0.50 | 0.50 | 0.50 |
| Fragrance | 0.15 | 0.15 | 0.15 | 0.15 | 0.15 | 0.15 | 0.15 | 0.15 |
| Hexylene Glycol | 2.00 | 2.00 | 2.00 | 2.00 | 2.00 | 2.00 | 2.00 | 2.00 |
| Vitamin E Acetate | 0.001 | 0.001 | 0.001 | 0.001 | 0.001 | 0.001 | 0.001 | 0.001 |

EXAMPLE 9

A clinical study was performed to evaluate the effectiveness of towelettes according to the present invention. The study investigated the effects of skin pH over a six hour period for three different types of alpha-hydroxy acid delivery systems. An untreated control site was evaluated against 4% glycolic acid active delivered via dermal patch, cream and towelette vehicles.

Thirteen male and female subjects (ages 30–50) participated. Each subject had two areas on each arm delineated as test sites for a total of four sites per subject. The dermal patch was worn for 8–10 hours prior to any measurement and left on the designated forearm site overnight for 8–10 hours. The glycolic acid formulation in a skin cream was applied to a second site at the rate of 2 mg/cm². Towelettes according to the present invention impregnated with the same level of glycolic acid were applied with a rubbing motion onto a third site of a subject's forearm. The fourth site was left untreated as a control. Skin pH and Skicon (percent moisture) measurements were taken on each test site initially for a baseline and then at hourly intervals up to 6 hours. Results of the study are reported in Tables II and III.

TABLE II

Skicon Moisture Readings

| TIME | CREAM | DERMAL PATCH | TOWELETTE | CONTROL |
| --- | --- | --- | --- | --- |
| Baseline | 601 | 153 | 626 | 34.1 |
| 1 hour | 138 | 110 | 98.2 | 40.4 |
| 2 hours | 83.1 | 66 | 45.6 | 29.5 |
| 3 hours | 55.9 | 40.7 | 39.7 | 32.1 |
| 4 hours | 45.1 | 43.9 | 37.4 | 23.2 |
| 5 hours | 33.4 | 33.5 | 28.4 | 19.2 |
| 6 hours | 29.6 | 26.1 | 27.4 | 15.3 |

TABLE III pH Study

| TIME | CREAM | DERMAL PATCH | TOWELETTE | CONTROL |
| --- | --- | --- | --- | --- |
| Baseline | 4.0 | 5.1 | 4.1 | 4.75 |
| 1 hour | 3.8 | 4.9 | 3.8 | 4.5 |
| 2 hours | 3.75 | 4.8 | 3.75 | 4.6 |
| 3 hours | 3.8 | 4.7 | 3.65 | 4.6 |
| 4 hours | 3.85 | 4.8 | 3.75 | 4.7 |
| 5 hours | 3.9 | 4.9 | 3.6 | 5.2 |
| 6 hours | 3.9 | 4.85 | 3.8 | 5.1 |

The study revealed that both the cream and towelette reduced skin pH. Decrease was maintained throughout the six hour period post application. A decrease in skin pH is indicative that the glycolic acid active has been deposited onto the skin and is operating in an effective mode.

The Skicon data one hour post application demonstrated that the cream induced the highest level of moisturization followed by the dermal patch and towelette. All three glycolic acid formulations moisturized better than the control.

The foregoing description and examples illustrate selected embodiments of the present invention. In light thereof variations and modifications will be suggested to one skilled in the art, all of which are within the spirit and purview of this invention.

What is claimed is:

1. A disposable towelette product for cleansing and managing signs of aging on the skin, the product comprising:
   (a) a container housing a towelette comprising:
      (i) a substrate which is a blend of rayon/polyester in a weight ratio ranging from 10:90 to 90:10;
      (ii) an alpha-hydroxycarboxylic acid; and
      (iii) a cosmetically acceptable vehicle for impregnating the alpha-hydroxycarboxylic acid as a composition onto the substrate;
   (b) written instructions on the package on use of the towelette against the skin to achieve a reduction in the signs of aging.

2. The towelette according to claim 1 wherein the alpha-hydroxycarboxylic acid is selected from the group consisting of glycolic, lactic, hydroxyoctanoic acids and mixtures thereof.

3. The towelette according to claim 1 further comprising a dimethicone copolyol in the impregnating composition.

4. The towelette according to claim 1 wherein the vehicle is water.

5. The towelette according to claim 1 wherein the composition further comprises from about 0.5 to about 95% of a polyol by weight of the impregnating composition.

6. The product according to claim 5 wherein the polyol is selected from the group consisting of glycerin, diglycerin, hexylene glycol, 2-methyl-1,3-propanediol, PPG-10 butanediol and mixtures thereof.

7. The towelette according to claim 6 wherein the amount of polyol present ranges from about 1.5 to about 20% by weight of the impregnating composition.

8. The towelette according to claim 1 wherein the substrate is a tissue folded in a Z-shaped formation.

9. A method for cleansing and managing the signs of aging on skin, the method comprising:
   (a) providing a towelette which is constituted of:
      (i) a substrate;
      (ii) an alpha-hydroxycarboxylic acid;
      (iii) a cosmetically acceptable vehicle for impregnating the alpha-hydroxycarboxylic acid as a composition onto the substrate; and
   (b) wiping the surface of the skin with the towelette.

* * * * *